(12) United States Patent
Stark et al.

(10) Patent No.: US 7,883,730 B2
(45) Date of Patent: Feb. 8, 2011

(54) RUMEN PROTECTED LYSINE

(75) Inventors: Peter A. Stark, Cottage Grove, MN (US); Mahmoud M. Abdel-Monem, Oak Harbor, WA (US)

(73) Assignee: Zinpro Corporation, Eden Prairie, MN (US)

( * ) Notice: Subject to any disclaimer, the term of this patent is extended or adjusted under 35 U.S.C. 154(b) by 60 days.

(21) Appl. No.: 12/468,141

(22) Filed: May 19, 2009

(65) Prior Publication Data

US 2009/0226559 A1   Sep. 10, 2009

Related U.S. Application Data

(62) Division of application No. 11/734,009, filed on Apr. 11, 2007.

(51) Int. Cl.
*A23K 1/18* (2006.01)
*A23J 1/02* (2006.01)
*A23K 1/17* (2006.01)
*C12P 13/08* (2006.01)

(52) U.S. Cl. .......................... 426/2; 426/657; 424/442; 435/115

(58) Field of Classification Search ........................ None
See application file for complete search history.

(56) References Cited

U.S. PATENT DOCUMENTS 3,993,795 A * 11/1976 Mauron et al. .............. 426/618
5,061,815 A    10/1991 Leu
5,885,610 A     3/1999 Anderson
6,770,640 B1    8/2004 Warshawsky et al.
2002/0037859 A1 3/2002 Flynn
2005/0130261 A1 6/2005 Wils et al.
2008/0255219 A1 10/2008 Stark et al.

FOREIGN PATENT DOCUMENTS

GB   1 380 274 A    1/1975
WO   98/12211 A1    3/1998

OTHER PUBLICATIONS

Li-Chan et al. "Covalent Attachment of Lysine to Wheat Gluten for Nutritional Improvement"; J. Agric. Food Chem., vol. 27, No. 4, pp. 877-882 (1979).*
Finot, et al., "N-Substituted Lysines as Sources of Lysine in Nutrition", Adv. Exp. Med. Bio. 1978; 105:549-570; Nutritional Improvement of Food and Feed Proteins, ed. by Friedman, published at Plenum, NY.
Finot, et al., "Availability of the True Schiff'S Bases of Lysine", Chemical Evaluation of the Schiff's Base Between Lysine and Lactose in Milk, Adv. Exp. Med. Biol. 1977; 86B:343-365.
Li-Chan, E. et al., "Covalent Attachment of Lysine to Wheat Gluten for Nutritional Improvement", J. of Agricultural and Food Chemistry, 2794:877-882 (1979).
Stark, International Search Report, PCT/US2008/052618 filed Jan. 31, 2008, 5 pages.

* cited by examiner

*Primary Examiner*—Robert A Wax
*Assistant Examiner*—Jeffrey T Palenik
(74) *Attorney, Agent, or Firm*—McKee, Voorhees & Sease, P.L.C.

(57) ABSTRACT

Use of lysine imines and compositions containing them as a source of rumen protected lysine for ruminant animals.

6 Claims, No Drawings

RUMEN PROTECTED LYSINE

CROSS-REFERENCE TO RELATED APPLICATIONS

This is a Divisional Application of U.S. application Ser. No. 11/734,009 filed Apr. 11, 2007, which application is hereby incorporated by reference in its entirety.

FIELD OF THE INVENTION

This invention relates to a rumen stable bioavailable dietary supplement for ruminant animals to provide in bioavailable form the essential amino acid lysine. It represents a specific improvement over the bypass rumen product of prior U.S. Pat. No. 5,885,610 to Anderson, owned by the common Assignee.

BACKGROUND OF THE INVENTION

It is well known that ruminants are in need of bioavailable essential amino acids in order to perform well as domesticated livestock. In this regard, if the animal, for example a dairy cow, does not have its minimum requirements of essential amino acids such as lysine and methionine, the animal will not produce milk at optimum yield, and its health may be in general decline.

Providing essential amino acids to ruminants is not as simple as it sounds. For example, the bacteria in the rumen of a cow are known to routinely degrade amino acid sources, like lysine and methionine. Put another way, the bacteria in the rumen metabolize the amino acid source and thus "rob" the animal of the benefit of the amino acid. By the time metabolized byproduct passes from the rumen into the intestine, the amino acid is gone. The challenge, therefore, is to develop products which will allow the amino acid to be stable in the rumen, but capable of absorption when it passes from the rumen into the intestine. In other words, the essential amino acids, such as lysine and methionine, need to be bioavailable only in the intestine, and remain stable and therefore not metabolized in the rumen.

In the past, this problem has been recognized, and feed developers have used fats, minerals, carbohydrates and binders to protect amino acids from rumen degradation. This technology involves simple coating of the material in hopes that the coated amino acid is rumen stable. Recently, Rhone Poulenc has provided a pH-sensitive polymer coating. The theory of a pH-sensitive polymer coating for the amino acid revolves around the pH differential between the rumen and the intestine. The rumen, for example, typically has a pH of 5.5 to 7.0, and the intestine a pH of 2-3. The theory of polymer-coated essential amino acids is that something which is stable as a coating at 5.5 to 7.0 (the rumen pH), but will solubilize at more acid pH's of the intestine (pH 2-3), should be stable in the rumen, but available in the intestine.

Both technologies used in the past, i.e. coatings, such as fat coatings, and the more recently developed pH-sensitive polymer coatings, have met with limited success and have some problems. The primary problem with any product relying upon coatings of any kind for rumen stability is that the coating can become abraded during handling and during chewing by the animal. If the process handler disturbs the coating, then the amino acid becomes available to microbes in the rumen and consumed, and therefore wasted by the animal. Likewise, if the animal abrades the coating during chewing, it then becomes available in the rumen for rumen bacteria to metabolize, and is therefore also wasted to the animal. Additionally, fat-protected or coated essential amino acids rely upon the fat resistance to enzymes in the rumen that are capable of digesting the protective fat coat, and, on the other hand, the ability of digestion by enzymes post-rumenally. However, if there is not a proper balance between resistance to attack in the rumen and digestion in the intestine, then the amino acid benefit to the animal may be lost.

From the above description, it can be seen that there is a real and continuing need for the development of products for delivery of essential amino acids to ruminant animals in a form that allows the material to be rumen stable, i.e. resistant to degradation in the rumen, but yet after delivery from the rumen to the intestine, highly absorbable and bioavailable in the intestine. It is a primary objective of this invention to improve upon available products to fulfill this need safely, effectively, efficiently and at low cost.

In the prior Zinpro Corporation patent by Michael Anderson, it was discovered that calcium or magnesium complexed salts of certain amino acids could be used to prepare a bypass rumen product. This invention takes a different attack on the problem with specificity of improving the availability of lysine for ruminants.

Lysine is an essential amino acid in the diet of mammals. That is, lysine cannot be synthesized by mammals at a rate adequate to meet metabolic requirements and so must be supplied in the diet. Corn (*Zea mays* L.) is notoriously low in lysine and, if used in a single grain ration, requires lysine supplementation both to maintain animal health and to achieve economical animal growth.

The present invention, by forming lysine compounds which are essentially immune to attack by the microbes in the rumen but can still be digested and absorbed through the intestine wall allow a highly bioavailable form of lysine that is surprisingly immune from rumen organism attack. Structures of the compounds prepared are centered around the imine of lysine (Schiff's base).

In the past, there have been some alpha imine and epsilon imine derivatives of lysine investigated for biologically available active derivatives for rats. See for example, Finot, *N-Substituted Lysines As Sources of Lysine in Nutrition*, Adv. Exp. Med. Bio. 1978; 105:549-570; Nutritional Improvement of Food and Feed Proteins, edited by Friedman, published at Plenum, New York, and Finot et al., *Availability of the true Schiff's bases of lysine. Chemical Evaluation of the Schiff's Base Between Lysine and Lactose in Milk*, Adv. Exp. Med. Biol. 1977; 86B:343-365. The first Finot article concludes that the biological availability of derivatives were four to seven times less reactive than free lysine in the Maillard reaction and could therefore be subjected to heat. The second article deals with chemical evaluation of the Schiff's base between lysine and the lactose in milk. There is no teaching in either article of any compounds having usefulness of providing stability of lysine derivatives in the rumen, nor providing compounds which can be successfully absorbed through the intestine after passing through the rumen to assure that lysine will be available to the animal for diet supplementation of this important essential amino acid.

It is therefore another primary objective to provide diet supplements for ruminants to provide lysine supplementation for animals that often use as a major grain ration corn (known to be notoriously low in lysine). As a result, overall economic growth of the animal can be enhanced, and enhanced in a manner which assures that the expense of lysine supplementation will go to the animal and not be "robbed" (so to speak) by the microbes in the rumen as the material passes through the rumen.

The method of achieving the above objectives with certain chemical structures premised around imine (Schiff's base) of lysine is another primary objective of the invention.

Yet another objective of the present invention is to provide compounds which can be utilized to achieve successfully a rumen bypass lysine supplement that does not rely upon encapsulation and one which employs compounds that are easily processible in feed forms.

BRIEF SUMMARY OF THE INVENTION

Use of lysine imines and compositions containing them as a source of rumen protected lysine for ruminant animals.

DETAILED DESCRIPTION OF THE PREFERRED EMBODIMENT

The basic concept in preferred form relates to the imine (Schiff's base) of lysine and some of its derivatives and salts. It could be the imines produced from aldehydes or ketones and the amino acid lysine. It could also be the imines from aldehydes or ketones and salts, estes, amides or complexes of lysine. In other words, the invention recognizes the imines of the lysine as rumen resistant sources of the essential amino acid lysine, and modification of other functional groups of lysine can be made, if one wishes, or not made if one wishes.

In the ruminant animal, ingested feed first passes into the rumen where it is partially broken down by bacterial fermentation. During rumen fermentation, rumen microbes utilize nitrogen from nitrogen compounds that they have degraded to form microbial protein. Nitrogen sources for rumen microbes include rumen degradable protein and peptides, free amino acids and urea. Microbial protein and undegraded feed protein pass to the abomasum and small intestine where hydrochloric acid and mammalian enzymes degrade microbial protein and undegraded feed protein to free amino acids and short peptides. The amino acids and short peptides are absorbed in the intestine, and the ruminant animals utilize the amino acids for synthesis of protein to sustain life, grow, reproduce and produce milk. However, if the amino acid, such as lysine, has been metabolized by rumen microbes, its value to the host animal is lost.

Of the twenty or more amino acids utilized by the animal to synthesize proteins, ten are considered to be essential. Examples of the essential amino acids include leucine, isoleucine, valine, methionine, threonine, lysine, histidine, phenylalanine and tryptophan. Essential amino acids are those amino acids which are required in quantities exceeding amounts produced by the animal, and must be supplied by microbial protein or rumen undegraded protein. Amino acids supplied in excess are degraded by the animal and excreted in the form of urea. The process of synthesizing urea from ammonia is a process requiring energy input from the animal. If certain essential amino acids are not provided in adequate amounts, the animal will be limited on the amount and types of protein it can produce, thus limiting animal performance. Supplying the proper amounts of essential amino acids therefore maximizes animal performance while enhancing efficiency of energy utilization by the animal.

Lysine and methionine are two of the most limiting essential amino acids when corn-based rations are fed. Results from studies also indicate that milk protein content is the most sensitive of the production variables (yield of milk, fat-corrected milk, milk protein, milk fat, and content of milk fat and protein) to alterations in amino acid content of duodenal digesta. Researchers have determined, by infusing incremental amounts of the limiting amino acids into the duodenum of lactating dairy cows, that the required contribution of lysine and methionine to total essential amino acids in duodenal digesta for maximum milk protein content approximated 15% and 5.2%, respectively.

This present invention relates to lysine imine and a companion invention relates in a broader sense to other imines, including some of the other essential amino acids, such as methionine. It is as another application being commonly assigned by the same inventors to Zinpro Corporation and filed simultaneously herewith. While this case preferably deals with lysine and its derivatives and salts, other alpha amino acids containing a terminal amino group may also be employed. An example is ornithine.

Compositions of the present invention which are rumen stable but intestine soluble for supplementing the diet of ruminants with a source of rumen protected lysine can generally be described as dietary supplement compositions that are imines (Schiff's base) of lysine. They can be an imine from a variety of aldehydes or ketones as evidenced by the examples below. The amino acid portion of the molecule could also be salts or esters or amides of the carboxylic acid. The alpha nitrogen could be a primary, secondary or tertiary amine or an amide. Generally speaking, the composition will contain a diet supplementing effective amount of a lysine imine of the formula:

(STRUCTURE 1)

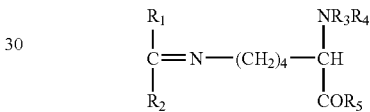

In the formula, the $R_1$ and $R_2$ moiety can be the same or different and can be connected or separate and selected from the group consisting of hydrogen, aliphatics, aromatics, and cyclic moieties. $R_3$ and $R_4$ can also be the same or different and can be selected from the group consisting of hydrogen, aliphatic, aromatics, and carbonyl moieties and where $R_3$ is carbonyl, $R_4$ is not present. $R_5$ can be —OH, or as previously indicated an ester producing moiety or a salt producing moiety or an amide producing moiety. The preferred structures are those wherein $R_1$ is hydrogen and $R_2$ is an aromatic, and $R_3$, $R_4$ are hydrogen and $R_5$ is —OH. The $R_3$, $R_4$ and $R_5$ (as —OH) can be other than hydrogen or with respect to $R_5$—OH, but it is mentioned herein that the scope of the invention includes hydrogen or alcohol moiety and other moieties as listed, primarily so that someone simply cannot substitute essentially any moiety at one of those positions and still achieve the benefit of the invention and argue non-infringement.

The preferred moieties at the $R_2$ position on the epsilon imine of lysine and are those formed from use as a reactant Benzaldehyde, Salicylaldehyde, cinnamaldehyde, or vanillin to prepare the most preferred compounds falling within the generic formula of structure 1 as herein set forth. These are shown below.

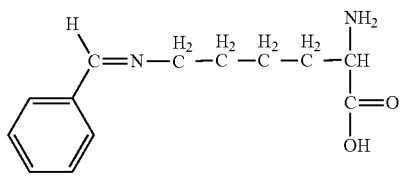

From Benzaldehyde

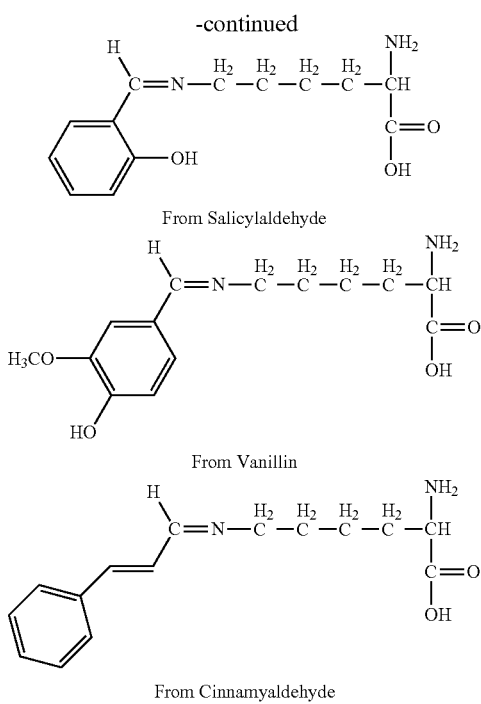

The compounds prepared above and especially those listed as preferred as easily processable. They can be sold and subdivided as a supplementing additive or they can be mixed with carriers to improve packaging, processability, and taste. Preferred carriers are, for example, powdered sugar which significantly improves taste for the ruminants that ingest the same. For example, the Benzaldehyde derivatives have an almond taste which can be masked with powdered sugar.

While it is preferred that the compounds of the present invention be added without additional carriers or filler material, as heretofore mentioned flavorants can be used as or with the carrier. If carriers are employed, the carrier can be suitable carriers such as distillers fermentation solubles, feed grains, corn cob flour, whey, or other cellulosic carrier materials. They can also be added at the same time as trace mineral preparations are added. In other words, they can be mixed with other nutritional ingredients.

The amount of supplement added to the feed ration will vary, of course, depending on whether one is using the pure compositions or the composition with a carrier. Basically the supplement will simply mix with the feed ration, as sold.

Generally the imines should be added at a level to provide sufficient lysine for the animals daily nutritional needs, i.e., within the range of about 1 gram to about 50 grams per animal per day.

The following examples illustrate the preparation of the imine (Schiff's base) of lysine of the present invention and illustrate a variety of different moieties that may be attached at the $R_1$ through $R_5$ position.

Example 1

Preparation of N-Benzylidene-L-Lysine from Lysine Hydrochloride and Benzaldehyde Lysine hydrochloride (4.8 g, 26.3 mmol) was dissolved in 35 mL of water. NaOH (1 g, 26.3 mmol) was added to the mixture which was cooled with an ice batch. To this mixture was added benzaldehyde (2.8 g, 26.3 mmol) and the product precipitated in about 10 minutes. The mixture was filtered and washed with water. The solid was dried to yield about 5.2 g of a white solid.

Example 2

Preparation of 2-amino-6-((E)-3-phenylallylideneamino)hexanoic from lysine hydrochloride and trans cinnamaldehyde Lysine hydrochloride (4.2 g, 23 mmol) was dissolved in 30 mL of water. NaOH (0.91 g, 23 mmol) was added to the mixture which was cooled with an ice batch. To this mixture was added trans cinnamaldehyde (3.0 g 23 mmol) and the product precipitated in about 10 minutes. The mixture was filtered and washed with water. The solid was dried to yield about 4.9 g.

Example 3

Preparation of 2-amino-6-(4-methoxybenzylideneamino)hexanoic acid from lysine hydrochloride and 4-hydroxy-3-methoxybenzaldehyde Lysine hydrochloride (2.2 g, 12 mmol) was dissolved in 25 mL of water. NaOH (0.48 g, 12 mmol) was added to the mixture which was cooled with an ice batch. To this mixture was added 4-methoxybenzaldehyde (1.6 g, 12 mmol) and the product precipitated in about 10 minutes. The mixture was filtered and washed with water. The solid was dried to yield about 2.6 g.

Example 4

Preparation of 2-amino-6-(octylideneamino)hexanoic acid from lysine hydrochloride and octylaldehyde Lysine hydrochloride (2.7 g, 14.8 mmol) was dissolved in 100 mL of water. NaOH (0.59 g, 14.8 mmol) was added to the mixture which was cooled with an ice batch. The pH was adjusted to between 4-5 by the addition of acetic acid. To this mixture was added octylaldehyde (1.9 g, 14.8 mmol) and the product precipitated in about 10 minutes. The precipitate agglomerated as an oil. The solvent was decanted off and the oil residue dried under vacuum. This yielded 2.5 g as an oil.

Example 5

Evaluation of Feeding N-Benzylidene-L-Lysine Using Lactating Holstein Dairy Cows

| | |
|---|---|
| TREATMENT DURATION: | 14 days |
| TREATMENTS: | 1) Control |
| | 2) Control plus 40 g Lys from N-Benzylidene-L-Lysine |

All cows received the same base diet. Cows were assigned to one of two treatments: (1) control, (2) control+N-Benzylidene-L-Lysine (TrTA). N-Benzylidene-L-Lysine was supplemented at a rate to supply 40 g of Lys when cows consumed 53.0 lb dry matter/d. The control diet was formulated to be deficient of lysine. The lactation response to the control diet as well as the diet supplemented with N-benzylidene-L-lysine is shown in Table 1. "P" refers to the probability value (p-value).

TABLE 1

Lactation responses to N-Benzylidene-L-Lysine

| Item | Control | Trt A | P |
|---|---|---|---|
| Milk, lbs/d | 73.7 | 77.3 | .1743 |
| FCM, lbs/d | 76.0 | 81.2 | .1074 |
| ECM, lbs/d | 75.9 | 81.3 | .0698 |
| Fat, % | 3.71 | 3.81 | .5358 |
| Fat, lbs/d | 2.72 | 2.94 | .1420 |
| Protein, % | 3.06 | 3.14 | .1478 |
| Protein, lbs/d | 2.25 | 2.41 | .0344 |
| SCC | 230.9 | 239.3 | .5014 |
| DMI, lbs/d | 53.5 | 53.1 | .8487 |
| ECM/Feed | 1.45 | 1.53 | .2562 |

From the Table 1 data, it can be concluded that the imine supplement composition produced more milk, more protein and more fat, and that the differences were significant as indicated by the P value. In contrast, if one were to simply add lysine to the diet, one would see no differences such as these, since microbes in the rumen would simply consume the lysine never allowing it to effectively supplement the animal and produce any different or enhanced result.

It therefore can be seen that the invention accomplishes at least all of its stated objectives.

What is claimed is:

1. The method of providing rumen protected lysine for dietary supplementation of ruminants, said method comprising:
    selecting at least one lysine imine to be used as a source of rumen protected lysine of the formula:

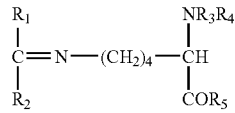
(STRUCTURE 1)

wherein $R_1$ and $R_2$ can be the same or different and are selected from the group consisting of hydrogen, aliphatic, aromatics, and cyclic moieties; $R_2$ is formed from use as a reactant Benzaldehyde, Salicylaldehyde, Cinnamaldehyde or Vanillin; $R_3$ and $R_4$ can be the same or different and are selected from the group consisting of hydrogen, aliphatic, aromatic and carbonyl moieties, and where $R_3$ is carbonyl, $R_4$ is not present and $R_5$ is selected from the group consisting of —OH, an ester producing moiety, an inorganic salt moiety and an amide producing moiety; and
    feeding the rumen protected lysine to a ruminant animal.

2. The method of claim 1 wherein $R_1$, $R_3$, and $R_4$ are hydrogen and $R_5$ is —OH.

3. The method of claim 1 wherein $R_3$, $R_4$ are hydrogen and $R_5$ is either an organic moiety to form an ester or an inorganic moiety to form a salt.

4. The method of claim 1 wherein an additional step includes mixing the lysine imine with a non-toxic carrier as a flavorant.

5. The method of claim 4 wherein the nontoxic carrier is selected from the group consisting of sugars, fermentations solubles, feed grains, corn cob flour, whey, and other cellulosic carrier materials.

6. The method of claim 5 wherein a diet supplementing effective amount of said lysine imine is used and is an amount sufficient to provide a level of from about 1 gram to about 50 grams of lysine used per animal per day.

* * * * *